United States Patent
Sakai et al.

(10) Patent No.: US 8,837,671 B2
(45) Date of Patent: Sep. 16, 2014

(54) RADIOGRAPHIC APPARATUS

(75) Inventors: Takihito Sakai, Kyoto (JP); Takayuki Sano, Takatsuki (JP)

(73) Assignee: Shimadzu Corporation, Kyoto (JP)

( * ) Notice: Subject to any disclaimer, the term of this patent is extended or adjusted under 35 U.S.C. 154(b) by 256 days.

(21) Appl. No.: 13/126,780

(22) PCT Filed: Oct. 30, 2008

(86) PCT No.: PCT/JP2008/069782
§ 371 (c)(1),
(2), (4) Date: Apr. 29, 2011

(87) PCT Pub. No.: WO2010/050032
PCT Pub. Date: May 6, 2010

(65) Prior Publication Data
US 2011/0206185 A1    Aug. 25, 2011

(51) Int. Cl.
*G01N 23/04* (2006.01)
*A61B 6/00* (2006.01)
*A61B 6/06* (2006.01)

(52) U.S. Cl.
CPC . *A61B 6/06* (2013.01); *A61B 6/487* (2013.01); *A61B 6/4021* (2013.01); *A61B 6/4429* (2013.01); *A61B 6/4452* (2013.01)
USPC .......................................... 378/62; 378/98.12

(58) Field of Classification Search
CPC .................................................... A61B 6/5241
USPC ............................................... 378/62, 98.12
See application file for complete search history.

(56) References Cited

U.S. PATENT DOCUMENTS

| 2008/0152088 A1* | 6/2008 | Wang et al. | 378/98.12 |
| 2008/0211902 A1 | 9/2008 | Ayaki | |
| 2009/0296880 A1* | 12/2009 | Beets et al. | 378/98.12 |

FOREIGN PATENT DOCUMENTS

| JP | 2004-57506 A | 2/2004 |
| JP | 2007-260027 A | 10/2007 |
| JP | 2007-275228 A | 10/2007 |
| JP | 2008-220 A | 1/2008 |
| JP | 2008-219428 A | 9/2008 |

OTHER PUBLICATIONS

International Search Report for the Application No. PCT/JP2008/069782 mailed Nov. 25, 2008.

* cited by examiner

*Primary Examiner* — Hoon Song
(74) *Attorney, Agent, or Firm* — Cheng Law Group, PLLC (57) ABSTRACT

This invention has one object to provide radiographic apparatus for acquiring a radioscopic image through superimposing of strip images. The radiographic apparatus allows prevention of blurring in the image with shortened imaging time for acquiring a clearer radioscopic image. According to the configuration of this invention, the FPD-4 is entirely within an imaging range throughout continuous taking of the strip images. In so doing, a minimum movement distance of the FPD-4 may be achieved in continuous taking of the strip images. Even when movement of the FPD-4 deviates from original setting, a range of the deviation may be suppressed to be small, since the movement distance of the FPD-4 is suppressed to be small. Consequently, superimposing of the strip images may realize acquisition of a clearer radioscopic image.

6 Claims, 8 Drawing Sheets

RADIOGRAPHIC APPARATUS

TECHNICAL FIELD

This invention relates to radiographic apparatus for generating a radioscopic image through irradiating a subject with radiation beams in a fan shape. More particularly, this invention relates to radiographic apparatus for generating a single radioscopic image through superimposing strip images.

BACKGROUND ART

Radiographic apparatus has various types of forms to acquire a radioscopic image through irradiating a subject with radiation. For instance, examples of the radiographic apparatus include one that allows generation of a clear radioscopic image through superimposing strip images. Such a method of acquiring an image is called slit imaging, and is well known (see, for example, Patent Literture 1).

Figure 13:
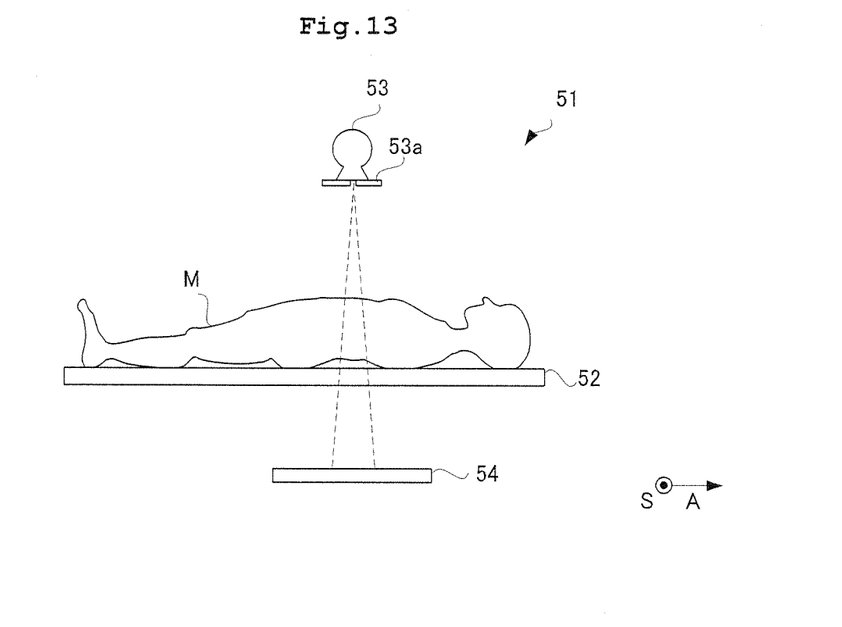
FIGS. 13 and 14 are plan views each showing X-ray apparatus according to a conventional configuration.

Now, description will be given hereinafter of a configuration in such radiographic apparatus. As shown in FIG. 13, the conventional radiography apparatus 51 includes a top board 52 for supporting a subject M placed thereon, a radiation source 53 above the top board 52, and a radiation detector (FPD) 54 below the top board 52. The radiation source 53 and the FPD 54 are movable along a body axis direction A of the subject M. The radiation source 53 has a collimator 53a attached thereto, whereby radiation is collimated to generate radiation beams in a fan shape.

Figure 14:
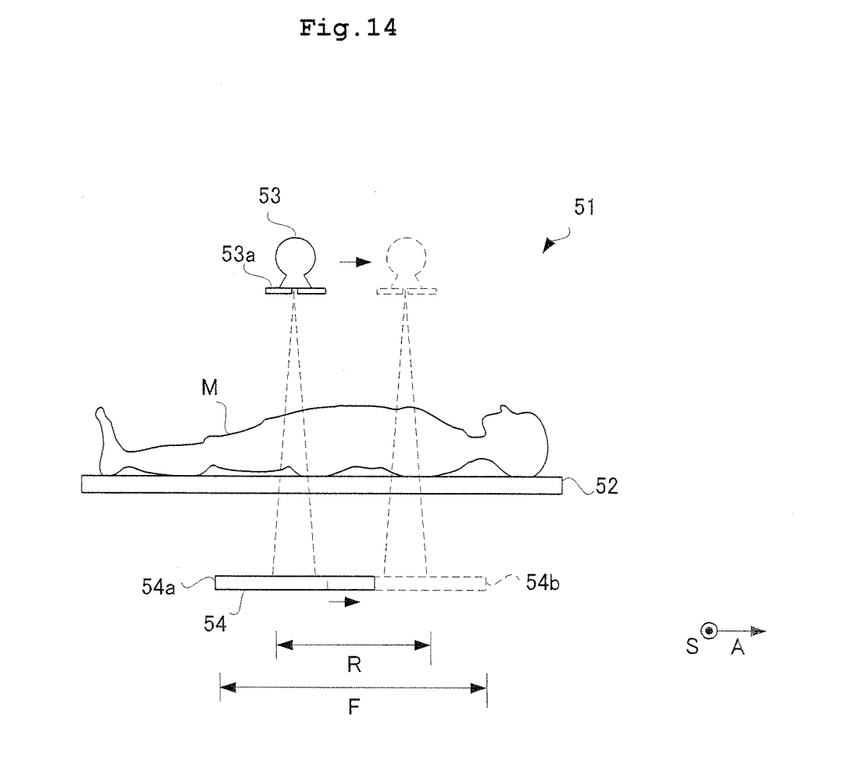

Firstly, in order to acquire a radioscopy image in the radiographic apparatus 51, the radiation source 53 and the FPD54 move synchronously while radiation beams are emitted intermittently. Here, as shown in FIG. 14, the radiation source 53 and the FPD 54 move along the body axis direction A of the subject M relative to the top board 52 while maintaining a relative positional relationship therebetween. Radiation beams transmit through the subject M and are detected with the FPD 54 in every irradiation therewith. Accordingly, a strip image is generated that extends in a body side direction S of the subject M. in every detection of radiation beams with the FPD 54.

Synchronous movement of the radiation source 53 and the FPD 54 causes deviation in a relative positional relationship of the radiation source 53, the FPD 54, and the subject M along the body axis direction A of the subject M. That is, each strip image has a different site of the subject M falling thereon.

Upon completion of irradiation with radiation beams, the strip images are superimposed one another while shifting, whereby a single radioscopic image is generated.

As is apparent from FIG. 14, radiation beams enter into the FPD 54 at an appropriately right angle. Accordingly, a clearer image may be acquired. Radiation emitted from the radiation source is divided into direct radiation linearly entering into the FPD 54, and indirect radiation entering into the FPD 54 having a modified traveling direction due to the subject M or the top board 52. Indirect radiation is obstructive to generation of a clear radioscopic image. Incidence of radiation into the FPD 54 at an appropriately right angle may realize elimination of the influence of indirect radiation. The radioscopic image is conventionally generated using only incident radiation into the FPD 54 at an appropriately right angle. Consequently, a clearer radioscopic image may be acquired under no influence of indirect radiation.

As above, a clearer radioscopic image may be acquired using only incident radiation into the FPD 54 at an appropriately right angle. On the other hand, however, only a small range of the subject M may be imaged with such radiation beams, and radiation beams are not usable for diagnosis as they are. Accordingly, stripe images are acquired through imaging two or more times and are superimposed for acquiring a radioscopic image having a fluoroscopy image of the subject M falling thereon in a wide range.

[Patent Literature 1]
Japanese Patent Publication No. 2008-219428

DISCLOSURE OF THE INVENTION

Problem to be Solved by the Invention

However, the conventional apparatus with such configuration has the following drawback. Specifically, according to the conventional configuration, a relative movement distance of the FPD 54 to the subject M is too long. As a result, the fluoroscopy images of the subject M falling on the strip images unexpectedly deviate and are superimposed one another, which leads to reduced visibility of the radioscopic image. In other words, the FPD 54 does not always move in accordance with a setting, but moves while deviating somewhat from the setting. Upon superimposing strip images, the FPD 54 should be deemed to move relative to the subject M in accordance with the setting. Consequently, the strip images are superimposed taking no consideration of the deviation. Then, the fluoroscopy images of the subject M falling on the strip images unexpectedly deviate in the body axis direction A of the subject M, which causes a blurred radioscopic image.

Moreover, another drawback arises that it takes a long time to acquire a radioscopic image. The longer distance the FPD 54 moves, the longer time it takes to complete taking of the strip images. Accordingly, a possibility increases that the subject M moves during imaging. Consequently, it is necessary to reduce an inspection time for acquiring a clearer radioscopic image.

This invention has been made regarding the state of the art noted above, and its object is to provide radiographic apparatus for acquiring a radioscopic image through superimposing of strip images. The radiographic apparatus allows prevention of blurring in the image with shortened imaging time, thereby acquiring a clearer radioscopic image.

Means for Solving the Problem

This invention is configured as stated below to achieve the above object. Specifically, radiographic apparatus of this invention includes a radiation source that moves freely along a given direction while applying radiation, a collimator for collimating radiation to generate fan shape radiation beams, and a radiation detecting device for detecting radiation beams, the radiation source moving along the given direction, whereby intermediate images being continuously taken over an imaging range, and each of the intermediate images having a portion of the imaging range falling thereon being superimposed one another, whereby a radioscopic image having the imaging range falling thereon being generated. Here, letting one forward end of the radiation detecting device in the given direction be a detecting device forward end, the other backward end of the radiation detecting device in the given direction be a detecting device backward end, one front end within the imaging range in the given direction be a range front end, and the other rear end within the imaging range in the given direction be a range rear end, the detecting device forward end thereof is aligned with the range front end in the given direction upon starting taking of the intermediate images, and the detecting device backward end thereof is aligned with the range rear end in the given direction upon completing taking of the intermediate images.

[Operation and Effect]

With the configuration of this invention, the movement distance of the radiation detecting device may be suppressed as much as possible upon continuously taking the intermediate images. Here, the detecting device forward end corresponds to the range front end of the imaging range. Accordingly, the radiation detecting device is entirely within the imaging range upon starting continuous imaging, and does not protrude beyond the range front end. Likewise, the radiation detecting device is entirely within the imaging range upon completing continuous imaging, and does not protrude beyond the range rear end. In other words, the radiation detecting device is entirely within the imaging range throughout continuous taking of the intermediate images. In so doing, a minimum distance may be achieved between the detecting device forward end upon starting continuous imaging and the detecting device backward end upon completing continuous imaging. That is, a minimum movement distance of the radiation detecting device may be achieved in continuous taking of the intermediate images. Even when the movement of the radiation detecting device deviates from the original setting, a range of the deviation may be suppressed to be small, since the movement distance of the radiation detecting device is suppressed to be small. Consequently, superimposing of the intermediate images may realize a clearer radioscopic image.

Moreover, a detector moving device is further provided for moving the radiation detector in the given direction. The detector moving device preferably moves the radiation detecting device during continuous taking of the intermediate images, and preferably moves the radiation detecting device up to a position where the detecting device backward end is aligned with the range rear end in the given direction upon completing continuous taking of the intermediate images.

[Operation and Effect]

With the foregoing configuration, a large imaging range may be achieved. Even when the imaging range extends, the radiation detector has a minimum movement distance. That is because the radiation detecting device moves up to a position where the detecting device backward end corresponds to the range rear end in the given direction upon completing continuous taking of the intermediate images.

Moreover, a radiation source moving device is further provided for moving the radiation source in the given direction upon starting foregoing continuous taking of the intermediate images. The radiation source is in an initial position, and thereafter moves during continuous taking of the intermediate images. The radiation source is in a termination position upon completing continuous taking of the intermediate images. Where the radiation source is in the initial position, an irradiation boundary of radiation beams to be applied forward in the given direction is aligned with the detecting device forward end of the radiation detecting device. Where the radiation source is in the termination position, an irradiation boundary of radiation beams to be applied backward in the given direction is aligned with the detecting device backward end of the radiation detecting device.

[Operation and Effect]

With the foregoing configuration, radiation beams may be always applied downward in a vertical direction relative to the radiation detecting device. The intermediate image is an image having a portion of the imaging range falling thereon. According to the foregoing configuration, the radiation source moves following movement of the intermediate image within the imaging range. Consequently, radiation beams may be always applied downward in a vertical direction relative to the radiation detecting device. In so doing, radiation enters into the radiation detecting device at an appropriately right angle, which may achieve a clearer radioscopic image.

Moreover, an inclining device is further provided for inclining the foregoing radiation source so as to be directed toward the detecting device forward end and the detecting device backward end. The radiation source is on a range front end side, and inclines such that radiation beams are directed toward the detecting device forward end upon starting continuous taking of the intermediate images. Where the intermediate images are continuously taken, the radiation source is once released from inclination, and is again inclined. Accordingly, the radiation source inclines such that radiation beams are directed toward the detecting device backward end upon completing continuous taking of the intermediate images.

[Operation and Effect]

The foregoing configuration is effective in the case where the imaging range is larger than the range where the radiation source may move. Specifically, the radiation source is on a range front end side, and inclines such that radiation beams are directed toward the detecting device forward end upon starting continuous taking of the intermediate images. The radiation source is on a rage rear end side, and inclines such that radiation beams are directed toward the detecting device backward end upon completing continuous taking of the intermediate images.

Such configuration may achieve a larger range for imaging. The radiation source is merely movable within a small range. As a result, the radiation detecting device cannot possibly move up to a position upward in the vertical direction in the detecting device forward end and the detecting device backward end. Accordingly, radiation beams cannot reach both ends of the imaging range. On the other hand, according to the foregoing configuration, the inclined radiation source allows radiation beams to positively reach both ends of the imaging range.

Effect of the Invention

According to the configuration of this invention, the radiation detecting device is entirely within the imaging range throughout continuous taking of the intermediate images. In so doing, a minimum movement distance of the radiation detecting device may be achieved in continuous taking of the intermediate images. Even when the movement of the radiation detector deviates from the original setting, a range of the deviation may be suppressed to be small, since the movement distance of the radiation detecting device is suppressed to be small. Consequently, superimposing of the intermediate images may realize a clearer radioscopic image. Moreover, the minimum movement distance of the radiation detecting device may realize suppression of an inspection time required for acquisition of a radioscopic image.

DESCRIPTION OF REFERENCES

R . . . range for imaging
Ra . . . range front end
Rb . . . range rear end
3 . . . X-ray tube (radiation source)
4 . . . FPD (radiation detecting device)
4a . . . FPD forward end (detecting device forward end)
4b . . . FPD backward end (detecting device backward end)
10 . . . inclination controller (inclination device)
12 . . . FPD movement controller (detector moving device)

EMBODIMENT 1

Embodiments of radiographic apparatus according to this invention will be described hereinafter with reference to the drawings. Here in the embodiments, description will be given of X-ray apparatus 1 using X-rays.

Figure 1:
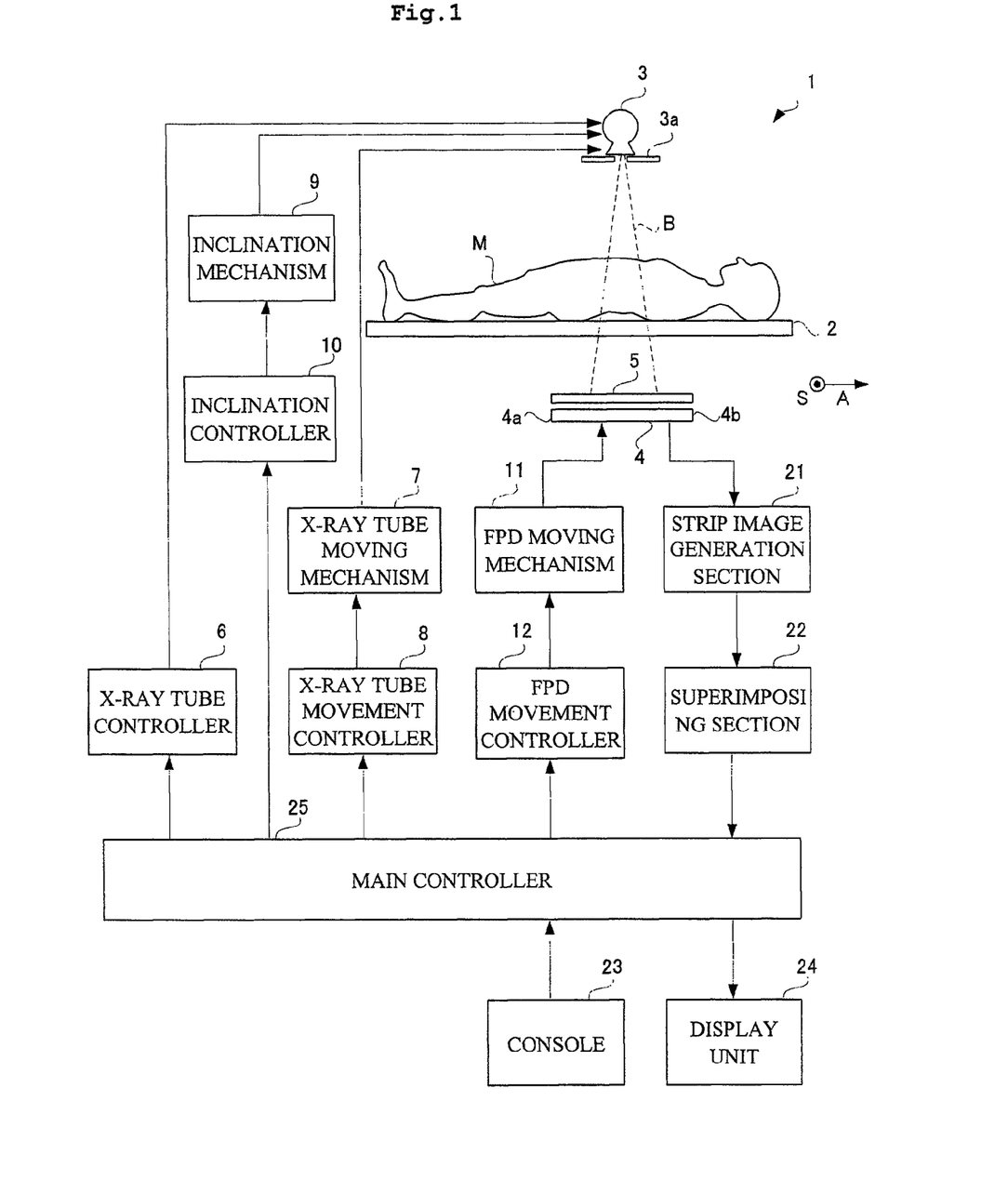
FIG. 1 is a functional block diagram showing a configuration of X-ray apparatus according to Embodiment 1.

Firstly, description will be given of a configuration of X-ray apparatus 1 according to Embodiment 1. FIG. 1 is a functional block diagram showing a configuration of X-ray apparatus according to Embodiment 1. As shown in FIG. 1, the X-ray apparatus 1 according to Embodiment 1 includes a top board 2 for supporting a subject M placed thereon, an X-ray tube 3 above the top board 2 for applying pulsed X-ray beams B, a flat panel detector (FPD) 4 below the top board 2 for detecting X-rays transmitting through the subject M, and an X-ray grid 5 for removing scattered X-rays entering into the FPD 4. Moreover, Embodiment 1 further includes an X-ray tube controller 6 for controlling tube voltage or tube current in the X-ray tube 3 and a temporal width of pulses in the X-ray beams B, an X-ray tube moving mechanism 7 for moving the X-ray tube 3 along a boxy axis direction A, and an X-ray tube movement controller 8 for controlling the X-ray tube moving mechanism 7. Moreover, Embodiment 1 further includes an inclination mechanism 9 for inclining the X-ray tube 3, and an inclination controller 10 for controlling the inclination mechanism 9. Moreover, the X-ray apparatus 1 according to Embodiment 1 further includes an FPD moving mechanism 11 for moving the FPD 4, and an FPD movement controller 12 for controlling the FPD moving mechanism 11.

In addition, the X-ray apparatus 1 includes a strip image generation section 21 for converting detection data outputted from the FPD 4 into a strip image, and a superimposing section 22 for superimposing the strip images to generate a fluoroscopic X-ray image. The X-ray tube corresponds to the radiation source in this invention. The FPD corresponds to the radiation detecting device in this invention. The strip image corresponds to the intermediate image in this invention. The inclination controller corresponds to the inclining device, and the X-ray tube moving mechanism to the radiation source moving device in this invention.

Moreover, the X-ray apparatus 1 includes a console 23 for inputting operator's instructions, and a display unit 24 for displaying the fluoroscopic X-ray image or animation.

The X-ray apparatus 1 also includes a main controller 25 for performing an overall control of the X-ray tube controller 6, the X-ray tube movement controller 8, the inclination controller 10, the strip image generation section 21, and the superimposing section 22. The main controller 25 has a CPU, and realizes the above components by executing various programs. The above components may be divided into arithmetic units that perform their functions.

Figure 2:
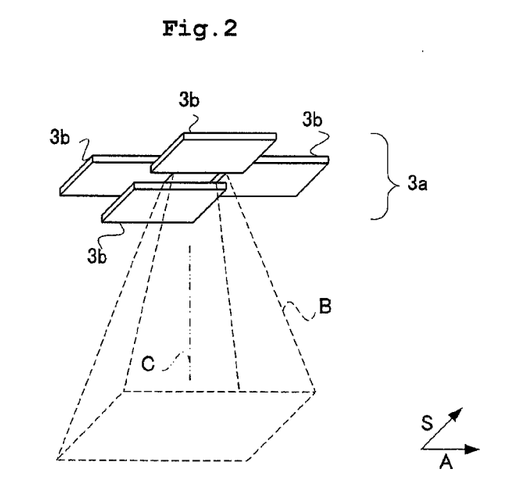
FIG. 2 is a perspective view showing a configuration of a collimator according to Embodiment 1.

The X-ray tube 3 irradiates the subject M with X-rays in accordance with control of the X-ray tube controller 6 with given tube current, tube voltage, and an irradiation time. As shown in FIG. 2, the X-ray tube 3 has a collimator 3a for collimating X-rays. The collimator 3a has one pair of leaves 3b that moves in a mirror-image symmetrical manner, and has one more pair of leaves 3b that similarly moves-in a mirror-image symmetrical manner. Adjustment of the collimator 3a may realize not only irradiation of an entire X-ray detection surface of the FPD 4 with X-ray beams B, and but also irradiation of only a center portion of the FPD 4 with X-ray beams B. Here, the X-ray beams B have a central axis C set therein. Each leaf 3b moves with reference to the central axis C in a mirror-image symmetrical manner.

The X-ray tube 3 is freely movable along the body axis direction A of the subject M (a longitudinal direction of the top board 2) in accordance with control of the X-ray tube movement controller 8. It is assumed that a forward limit position in the range where the X-ray tube 3 may move in the body axis direction A be a front limit position, and a backward limit position be a rear limit position. Here, the body axis direction of the subject corresponds to the given direction in this invention.

The X-ray tube 3 may incline from one end to the other end of the body axis direction A of the subject M on the top board 2 in accordance with control of the inclination controller 10.

The FPD 4 is freely movable along the body axis direction A of the subject M (a longitudinal direction of the top board 2) in accordance with control of the FPD movement controller 12. The FPD 4 has two ends in the body axis direction A, letting one forward end of the two ends be the FPD forward end 4a and the other backward end be the FPD backward end 4b (see FIG. 1.) The X-ray grid 5 follows the FPD 4. Here, the FPD forward end and the FPD backward end correspond to the detecting device forward end and the detecting device backward end, respectively, in this invention. Moreover, the FPD movement controller corresponds to the detector moving device in this invention.

Figure 3:
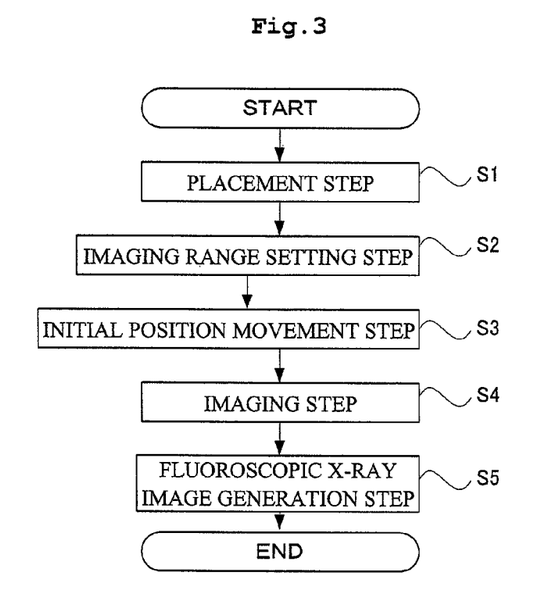
FIG. 3 is a flow chart showing operations of the X-ray apparatus according to Embodiment 1.

Next, description will be given hereinafter of operations of the X-ray apparatus having such configuration. FIG. 3 is a flow chart illustrating operations of the X-ray apparatus according to Embodiment 1. A method of taking a fluoroscopic X-ray image with X-ray apparatus includes a placement step S1 for placing a subject M on a top board 2; an imaging range setting step S2 for setting an imaging range R; an initial position movement step S3 for moving an X-ray tube 3 and an FPD 4 to an initial position; an imaging step S4 for continuously taking strip images while moving the X-ray tube 3 and the FPD 4 to a termination position; and a fluoroscopic X-ray image generation step S5 for generating a fluoroscopic X-ray image through superimposing the strip images. Details of each of these steps will be described in order.

<Placement Step S1, Imaging Range Setting Step S2>

Figure 4:
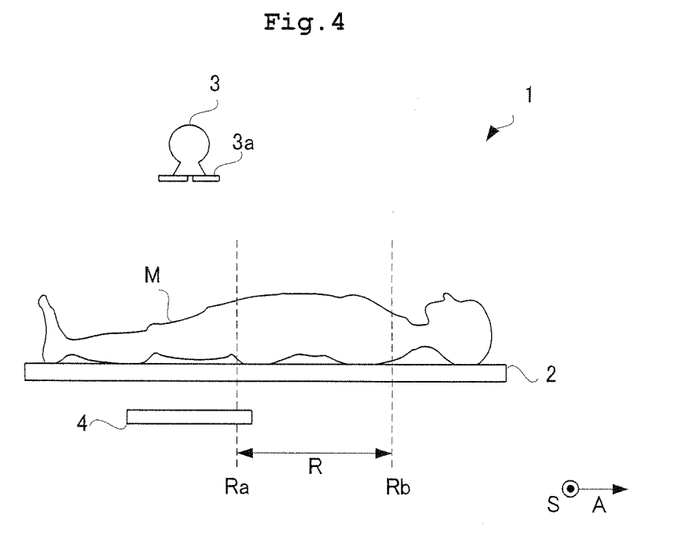
FIG. 4 through 6 are plan views each showing operations of the X-ray apparatus according to Embodiment 1.

Firstly, the subject M is placed on the top board 2. Thereafter, an operator may set a size of a fluoroscopic X-ray image to be imaged via a console 23. The set size of the fluoroscopic X-ray image corresponds to the imaging range R. For instance, as shown in FIG. 4, it is assumed that the imaging range R is set from an upper chest to a waist of the subject M. Here, let one forward end of the two ends of the imaging range R in the body side direction A be the range front end Ra, and the other backward end be the range rear end Rb. In Embodiment 1, the range front end Ra corresponds to the waist of the subject M. The range front end Ra is not limited to this. The range rear end Rb may correspond to the upper chest of the subject M.

<Initial Position Movement Step S3>

Figure 5:
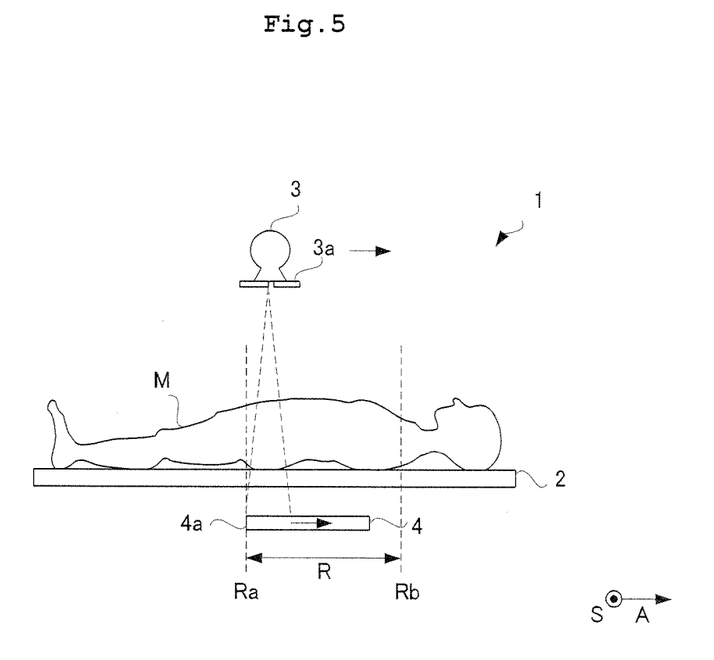

At that time when an operator provides instructions to start imaging, the X-ray tube movement controller 8 controls the X-ray tube 3 and moves the X-ray tube 3 into a position on a range rear end Ra side. On the other hand, the FPD movement controller 12 controls and moves the FPD 4. Accordingly, the position of the FPD front end 4a of the FPD 4 in the body axis direction A is aligned with the range front end Ra. This position is an initial position of the X-ray tube 3 and the FPD 4. This state of the X-ray apparatus 1 is as shown in FIG. 5.

<Imaging Step S4>

The X-ray tube 3 irradiates the subject with X-ray beams B in a fan shape spreading in a body side direction S' of the subject M downward in the vertical direction through control of the X-ray tube controller 6. Here, an irradiation boundary of radiation beams B in the forward body axis direction A where X-rays reach is aligned with the FPD forward end 4a of the FPD 4. Thereafter, the FPD 4 detects X-ray beams B emitted from the subject M, and sends detection signals to the strip image generation section 21. The strip image generation section 21 generates elongated strip images extending in the body side direction S of the subject M based on detection signals. The strip image is an image having a fluoroscopic image of the subject M as a portion of the imaging range falling thereon.

Subsequent to this, the X-ray tube 3 and the FPD 4 move from the respective initial position. The X-ray tube 3 intermittently applies X-ray beams B in a fan shape. The strip image is generated in every irradiation with X-ray beams, and the strip images are superimposed one another and sent to the superimposing section 22.

Figure 6:
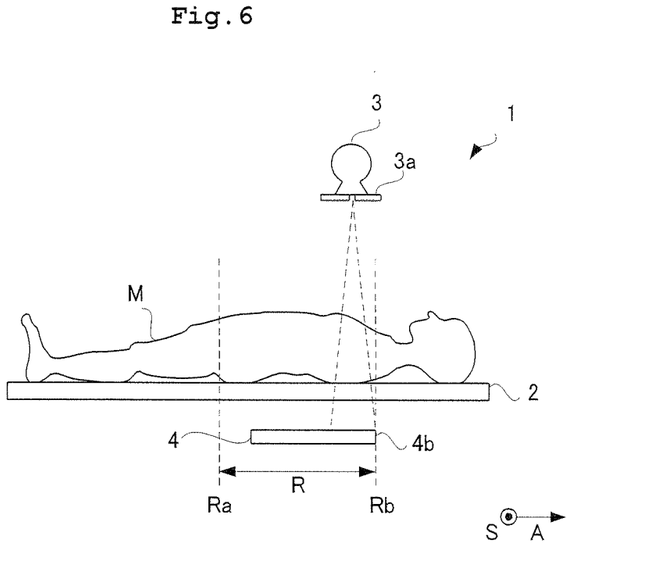

Subsequently, as shown in FIG. 6, the FPD 4 stops moving at a position where the FPD backward end 4b of the FPD 4 in the body axis direction A is aligned with the range rear end Rb. Here, the X-ray tube 3 moves and stops on a range rear end Rb side. This corresponds to the termination position of the X-ray tube 3 and the FPD 4. Thereafter, the X-ray tube 3 applies X-ray beams B for generating the last strip image. Here, an irradiation boundary in the backward body axis direction A where X-rays reach is aligned with the FPD backward end 4b of the FPD 4.

<Fluoroscopic X-ray Image Generation Step S5>

Subsequently, a fluoroscopic X-ray image of the subject M is generated through superimposing strip images. Specifically, the strip images are arranged in time sequence of imaging, and they are superimposed one another. The strip images adjacent to one another in time sequence include the same portion of the subject M. Accordingly, deviation and superimposing of the strip images lead to overlap of the same portion in the subject M, whereby a single fluoroscopic X-ray image is generated. The display unit 24 displays a fluoroscopic X-ray image formed in such manner. Then, acquisition of a fluoroscopic X-ray image is completed.

Figure 7:
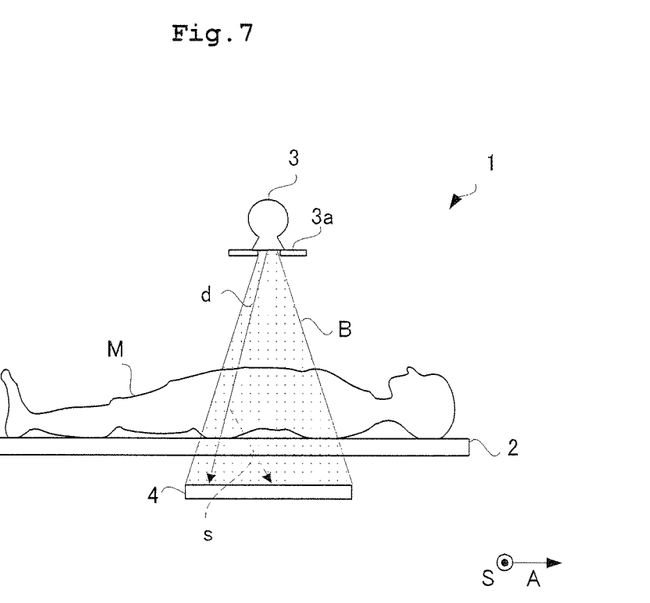
FIGS. 7 and 8 are plan views each showing a scattered X-ray according to Embodiment 1.

Now, simple description will be given of a principle that avoids the influence of scattered X-rays in Embodiment 1. FIG. 7 shows a case where wide X-ray beams B in a cone shape in the body axis direction A are applied. Direct X-rays d in FIG. 7 enter into the FPD 4. Supposing that indirect X-rays s occur on paths of the direct X-rays d, the indirect X-rays s enter into the FPD 4, which leads to reduced visibility of the fluoroscopic X-ray image.

Figure 8:
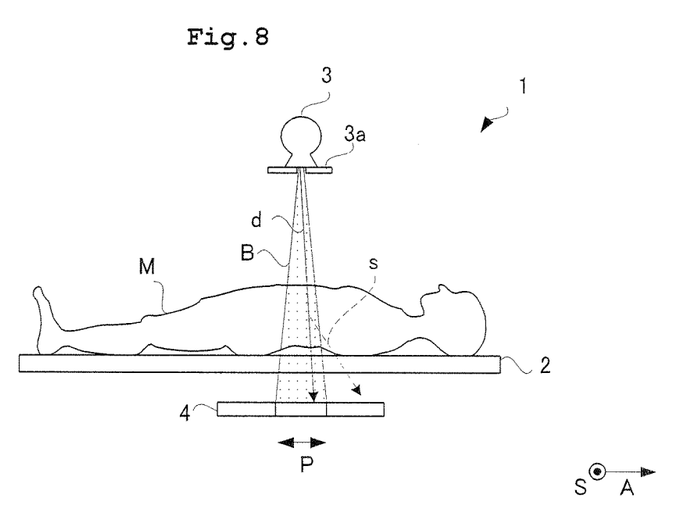

Consequently, Embodiment 1 has a configuration as shown in FIG. 8 that X-ray beams B are narrower in body axis direction A than the collimator 3a. Only detection data is used for the strip images that is acquired from a portion P of the FPD 4 where X-ray beams B are applied. The portion P is determined with reference to the X-ray tube 3, and is in the same position as the X-ray tube 3 in body axis direction A. Accordingly, direct X-rays d may enter into the portion P, whereas indirect X-rays s cannot enter into the portion P. That is because indirect X-rays s tend to extremely differ from direct X-rays d in traveling direction, and divert the portion P. Thus, the influence of indirect X-rays may be avoided in the strip images.

Moreover, Embodiment 1 has various types of forms of imaging through adjusting the collimator 3a. For instance, the collimator 3a may open for taking a fluoroscopic X-ray image with X-ray beams B in a cone shape, as shown in FIG. 7.

With the configuration of Embodiment 1 as above, the movement distance of the FPD 4 may be suppressed as much as possible upon continuously taking the strip images. Here, the FPD forward end 4a is aligned with the range front end Ra of the imaging range R. Accordingly, the FPD 4 is entirely within the imaging range R upon starting continuous imaging, and does not protrude beyond the range front end Ra, as shown in FIG. 5. Likewise, the FPD 4 is entirely within the imaging range R upon completing continuous imaging, and does not protrude beyond the range rear end Rb, as shown in FIG. 6. In other words, the FPD 4 is entirely within the imaging range R throughout continuous taking of the intermediate images. In so doing, a minimum distance may be achieved between the FPD forward end 4a upon starting continuous imaging and the FPD backward end 4b upon completing continuous imaging. That is, a minimum movement distance of the FPD 4 may be achieved in continuous taking of the strip images. Even when the movement of the FPD 4 deviates from the original setting, a range of the deviation may be suppressed to be small, since the movement distance of the FPD 4 is suppressed to be small. Consequently, superimposing of the strip images may realize a clearer radioscopic image.

According to the configuration of Embodiment 1, even when the imaging range R extends due to increased movement distance of the FPD 4, the FPD 4 has a minimum movement distance. That is because the FPD 4 moves up to a position where the FPD backward end 4b is aligned with the range rear end Rb in the given direction upon completing continuous taking of the strip images.

Moreover, according to the configuration of Embodiment 1, X-ray beams B are always applied downward in the vertical direction relative to the FPD 4. The strip image is an image having a portion of the imaging range R falling thereon. With the configuration of Embodiment 1, the X-ray tube 3 moves following movement of the strip image within the imaging range R. Consequently, X-ray beams B are always applied downward in the vertical direction relative to the FPD 4. In so doing, the strip images are not influenced by scattered X-rays, which may achieve a clearer fluoroscopic X-ray image.

Finally, an effect of the configuration in Embodiment 1 is to be emphasized with reference to FIG. 14 showing the conventional configuration. In FIG. 14, a distance F between the FPD forward end 54a upon starting continuous imaging and the FPD backward end 54b upon completing continuous imaging is larger than the imaging range R. That is because the radiation source 53 and the FPD 54 move synchronously while maintaining the positional relationship therebetween. In Embodiment 1, the distance F between the FPD forward end 54a upon starting continuous imaging and the FPD backward end 54b upon completing continuous imaging is aligned with the imaging range R. Accordingly, it can be seen that the moving distance of the FPD 4 is reduced as compared with the conventional configuration.

This invention is not limited to the foregoing embodiment, but may be modified as follows.

Figure 9:
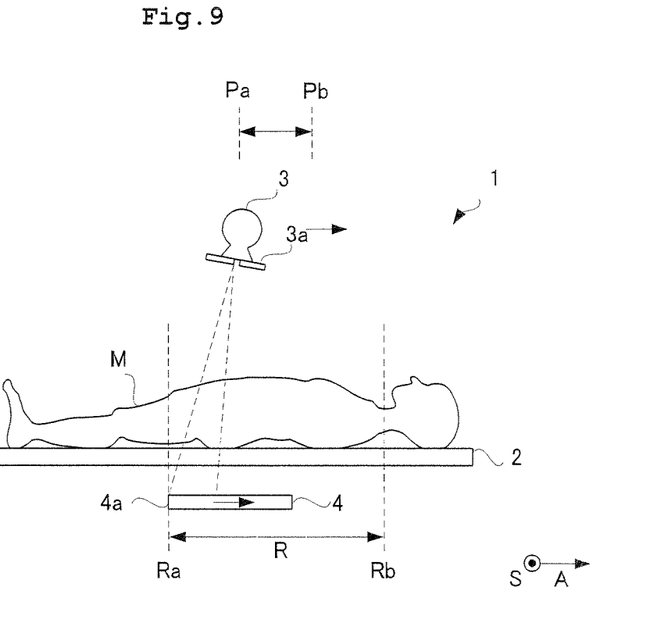
FIG. 9 through 12 are plan views each showing configurations of X-ray apparatus according to one modification of this invention.
Figure 10:
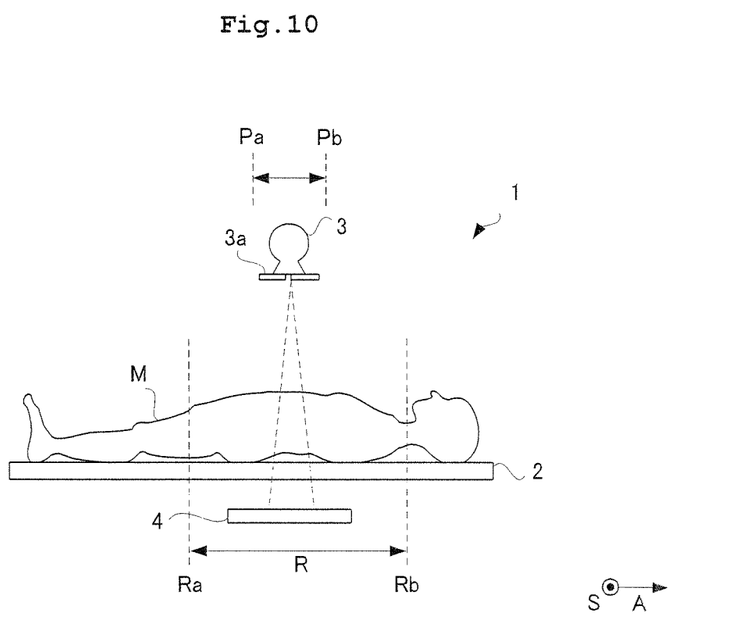
Figure 11:
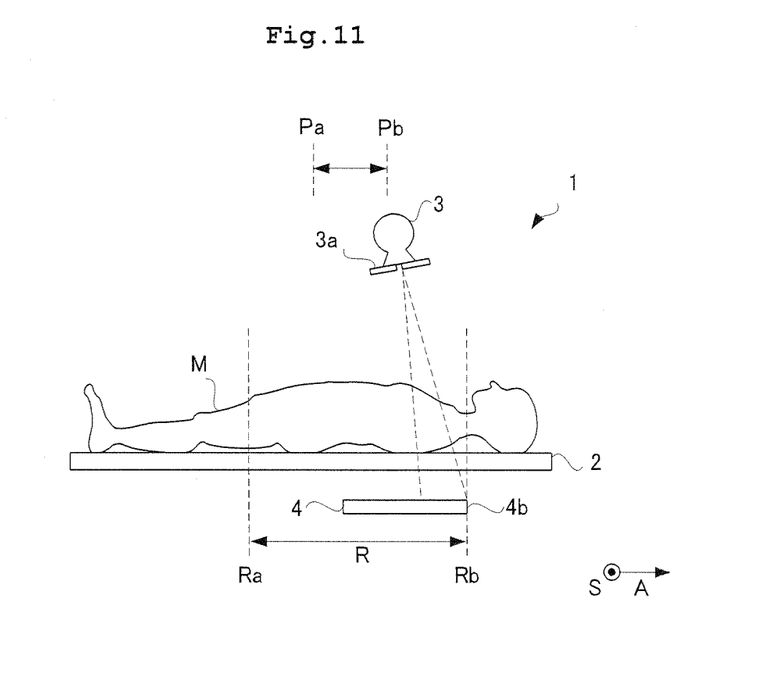

The X-ray tube 3 irradiates the FPD 4 with X-ray beams B downward in the vertical direction at the initial and termination positions in the foregoing embodiment. However, this invention is not limited to such configuration. The X-ray tube 3 may incline at the initial and termination positions. The specific configuration thereof is to be described. Specifically, as shown in FIG. 9, the X-ray tube 3 moves to an initial position P1 upon completion of the initial position movement step S3. Moreover, the X-ray tube 3 inclines so as to be directed toward the FPD forward end 4a with the inclination mechanism 9. Here, an irradiation boundary of X-ray beams B in the forward body axis direction A where X-rays reach is aligned with the FPD forward end 4a of the FPD 4. This state proceeds to the imaging step S4. In the imaging step S4, the X-ray tube 3 and the FPD 4 move along the body axis direction A of the subject M. Accordingly, the X-ray tube 3 is gradually released from inclination by the inclination mechanism 9. In the case where the center portion of the imaging range R is imaged, the X-ray tube 3 is completely released from inclination, and irradiates the FPD 4 with X-ray beams B downward in the vertical direction. The X-ray tube 3 inclines so as to be gradually directed toward the FPD backward end 4b of the FPD 4 as taking of the strip images proceeds from this state. Upon moving to the termination position P2 of the X-ray tube 3, the X-ray tube 3 inclines so as to be directed toward the FPD forward end 4a by the inclination mechanism 9, as shown in FIG. 11. Here, an irradiation boundary of X-ray beams B in the forward body axis direction A where X-rays reach is aligned with the FPD backward end 4b of the FPD 4.

Such configuration may achieve a larger imaging range R. The movable range R where the X-ray tube 3 may move is merely within a small range from the initial position P1 to the termination position P2. As a result, the X-ray tube 3 cannot possibly move up to a position upward in the vertical direction in the FPD forward end 4a and the FPD backward end 4b. Accordingly, X-ray beams B cannot reach both ends of the imaging range R. On the other hand, according to this modification, the inclined X-ray tube 3 allows X-ray beams B to positively reach both ends of the imaging range R. It may also be assumed that the initial position P1 of the X-ray tube 3 be the front limit position of the X-ray tube 3 mentioned above, and the termination position P2 of the X-ray tube 3 be the rear limit position mentioned above.

Figure 12:
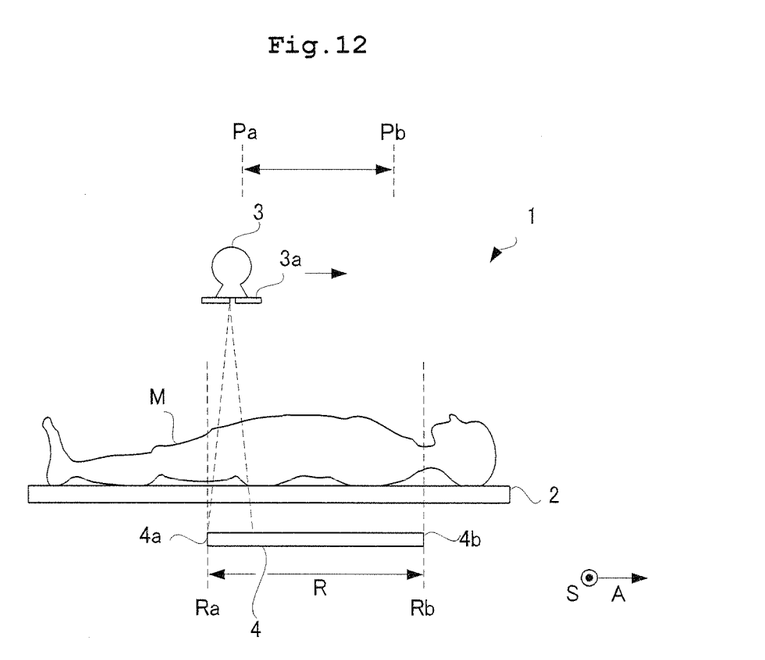

(2) The FPD 4 is movable in the imaging step S4 in the foregoing embodiment. This invention is not limited to this. That is, the FPD 4 may be configured not to move. Specifically, as shown in FIG. 12, the FPD forward end 4a of the FPD 4 is aligned with the range front end Ra in the imaging range R in body axis direction A, and the FPD forward end 4b of the FPD 4 is aligned with the range rear end Rb in the imaging range R in body axis direction A. Consequently, the effect of this invention may be provided without moving the FPD 4.

(3) The foregoing embodiment discusses a medical apparatus. This invention is applicable also to apparatus for industrial use and for the nuclear field.

INDUSTRIAL UTILITY

As described above, this invention is suitable for medical instruments.

The invention claimed is:

1. Radiographic apparatus comprising:
    a radiation source that moves freely along a given direction while applying radiation,
    a collimator for collimating radiation to generate fan shape radiation beams;
    a radiation detecting device for detecting the radiation beams; and
    a main controller comprising a CPU,
    wherein the CPU comprises a program that moves the radiation source along the given direction, provides for intermediate images to be continuously taken over an imaging range, each of the intermediate images having a portion of the imaging range falling thereon being superimposed on one another, and provides for a radioscopic image having the imaging range falling thereon to be generated, and
    wherein letting one forward end of the radiation detecting device in the given direction be a detecting device forward end, the other backward end of the radiation detecting device in the given direction be a detecting device backward end, one front end within the imaging range in the given direction be a range front end, and the other rear end within the imaging range in the given direction be a range rear end, the CPU comprises a program that aligns the detecting device forward end with the range front end in the given direction upon starting taking of the intermediate images, whereby an area irradiated with radiation on the radiation detecting device is located adjacent to the detecting device forward end, and that aligns the detecting device backward end with the range rear end in the given direction upon completing taking of the intermediate images, whereby the area irradiated with radiation on the radiation detecting device is located adjacent to the detecting device backward end, each of the intermediate images being narrower than the entire radiation detector relative to the given direction.

2. The radiographic apparatus according to claim 1, further comprising a detector moving device,
    wherein the CPU comprises a program that controls the detector moving device to move the radiation detector in the given direction such that the radiation detecting device is moved during continuous taking of the intermediate images, and is moved up to a position where the detecting device backward end is aligned with the range rear end in the given direction upon completing continuous taking of the intermediate images.

3. The radiographic apparatus according to claim 1, further comprising a radiation source moving device,
    wherein the CPU comprises a program that controls the radiation source moving device to move the radiation source in the given direction upon starting foregoing continuous taking of the intermediate images, such that the radiation source is in an initial position, and thereafter is moved during continuous taking of the intermediate images, and is in a termination position upon completing continuous taking of the intermediate images,
    an irradiation boundary of radiation beams to be applied forward in the given direction being aligned with the detecting device forward end of the radiation detecting device where the radiation source is in the initial position, and
    an irradiation boundary of radiation beams to be applied backward in the given direction being aligned with the detecting device backward end of the radiation detecting device where the radiation source is in the termination position.

4. The radiographic apparatus according to claim 3, further comprising an inclining device,
wherein the CPU comprises a program that controls the inclining device to incline the radiation source so as to be directed toward the detecting device forward end and the detecting device backward end, such that the radiation source is on a range front end side, and inclined such that radiation beams are directed toward the detecting device forward end upon starting continuous taking of the intermediate images, is once released from inclination and again inclined where the intermediate images are continuously taken, and is inclined such that radiation beams are directed toward the detecting device backward end upon completing continuous taking of the intermediate images.

5. The radiographic apparatus according to claim 2, further comprising a radiation source moving device,
wherein the CPU comprises as program that controls the radiation source moving device to move the radiation source in the given direction upon starting foregoing continuous taking of the intermediate images, such that the radiation source is in an initial position, and thereafter is moved during continuous taking of the intermediate images, and is in a termination position upon completing continuous taking of the intermediate images,
an irradiation boundary of radiation beams to be applied forward in the given direction being aligned with the detecting device forward end of the radiation detecting device where the radiation source is in the initial position, and
an irradiation boundary of radiation beams to be applied, backward in the given direction being aligned with the detecting device backward end of the radiation detecting device where the radiation source is in the termination position.

6. The radiographic apparatus according to claim 5, further comprising an inclining device,
wherein the CPU comprises a program that controls the inclining device to incline the radiation source so as to be directed toward the detecting device forward end and the detecting device backward end, such that
the radiation source is on a range front end side, and inclined such that radiation beams are directed toward the detecting device forward end upon starting continuous taking of the intermediate images, is once released from inclination and again inclined where the intermediate images are continuously taken, and is inclined such that radiation beams are directed toward the detecting device backward end upon completing continuous taking of the intermediate images.

\* \* \* \* \*